(12) United States Patent
Clopp

(10) Patent No.: US 10,598,868 B2
(45) Date of Patent: Mar. 24, 2020

(54) SEALING A FIBER BUNDLE END WITH GLASS FRITTING

(71) Applicant: INTUITIVE SURGICAL OPERATIONS, INC., Sunnyvale, CA (US)

(72) Inventor: Mathew Clopp, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/459,452

(22) Filed: Jul. 1, 2019

(65) Prior Publication Data

US 2019/0324216 A1 Oct. 24, 2019

Related U.S. Application Data

(62) Division of application No. 15/956,942, filed on Apr. 19, 2018, now Pat. No. 10,379,297.

(Continued)

(51) Int. Cl.
 *G02B 6/38* (2006.01)
 *G02B 6/42* (2006.01)
(Continued)

(52) U.S. Cl.
 CPC ......... *G02B 6/3855* (2013.01); *G02B 6/3644* (2013.01); *G02B 6/4248* (2013.01); *A61B 1/00167* (2013.01); *G02B 6/4415* (2013.01)

(58) Field of Classification Search
 CPC ................................. G02B 6/04; G02B 6/3855
 See application file for complete search history.

(56) References Cited

U.S. PATENT DOCUMENTS 3,681,164 A * 8/1972 Bazinet, Jr. et al. ... C03B 37/15
 156/294
4,648,892 A * 3/1987 Kittrell .................. A61B 17/22
 600/342

(Continued)

FOREIGN PATENT DOCUMENTS

JP 57042006 A * 3/1982 ............... G02B 6/06
JP 57097503 A * 6/1982 ............... G02B 6/04

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Daniel Petkovsek
(74) *Attorney, Agent, or Firm* — Haynes and Boone, LLP

(57) ABSTRACT

An apparatus comprises a housing having a first melting temperature and a fiber bundle extending through the housing. The fiber bundle comprises a plurality of fibers having a second melting temperature. An end of each of the plurality of fibers extends past an edge of the housing. The apparatus further comprises a first seal between the plurality of fibers themselves and a second seal between the plurality of fibers and an inner surface of the housing. The seals each comprise a glass material having a third melting temperature lower than the first two melting temperatures. The second seal is configured to be formed as a result of the fiber bundle being inserted into the housing. The glass material coats a tip of each of the plurality of fibers and at least a portion of a side of each of the plurality of fibers near an end of the fiber bundle.

20 Claims, 5 Drawing Sheets

Related U.S. Application Data

(60) Provisional application No. 62/488,118, filed on Apr. 21, 2017.

(51) Int. Cl.
*G02B 6/36* (2006.01)
*A61B 1/00* (2006.01)
*G02B 6/44* (2006.01)

(56) References Cited

U.S. PATENT DOCUMENTS

| | | | | |
|---|---|---|---|---|
| 5,208,890 A | * | 5/1993 | Kohler | G02B 6/04 385/115 |
| 5,472,471 A | * | 12/1995 | Baba | G02B 6/04 501/10 |
| 6,396,995 B1 | * | 5/2002 | Stuelpnagel | G01N 21/253 385/115 |
| 6,978,074 B2 | * | 12/2005 | Shu | F23D 14/725 385/115 |
| 7,460,755 B2 | * | 12/2008 | Bruesselbach | G02B 6/04 385/115 |
| 8,702,291 B2 | * | 4/2014 | Stephan | G02B 6/0008 362/259 |
| 1,037,929 A1 | | 8/2019 | Clopp | |
| 2006/0165358 A1 | * | 7/2006 | Trebst | G02B 6/04 385/115 |
| 2013/0108221 A1 | * | 5/2013 | Xie | G02B 6/3644 385/82 |

* cited by examiner

SEALING A FIBER BUNDLE END WITH GLASS FRITTING

CROSS-REFERENCE TO RELATED APPLICATIONS

This application is a division of U.S. patent application Ser. No. 15/956,942 filed Apr. 19, 2018 which claims the benefit of U.S. Provisional Application 62/488,118 filed Apr. 21, 2017, all of which are incorporated by reference herein in their entirety.

FIELD

The present disclosure is directed to medical devices and methods for manufacturing medical devices. More particularly, the present disclosure is directed to systems and methods for sealing an end of an optical fiber bundle using glass fritting.

BACKGROUND

Fiber optic bundles may be used in various applications that involve the transmission of light. A fiber optic bundle is an assembly of multiple optical fibers, each of which is capable of transmitting light from one end of the optical fiber to the other end. Many different types of medical instruments use fiber optic bundles for illumination, imaging, or both. An endoscope is one example of a medical instrument that uses fiber optic bundles. For example, an endoscope may be used to look inside the body at a particular internal organ. The endoscope may include a fiber optic bundle for directing light towards the internal organ. The endoscope may also include a fiber optic bundle for capturing and carry an image of the internal organ to an eyepiece or some other type of image viewer.

Assembling multiple optical fibers to form a fiber optic bundle typically includes terminating the optical fibers at an end of the fiber optic bundle. As one example, a fiber optic bundle may be terminated by potting the optical fibers with a polymer adhesive. The polymer adhesive is cured to hold the optical fibers together and form a barrier at the end of the fiber optic bundle. Further, a sterilization cleaning process may be performed on the fiber optic bundle. This sterilization cleaning process typically involves multiple autoclave cycles that produce heat and steam that can cause the polymer adhesive to break down. Consequently, currently available polymer adhesives may not provide a barrier with the level of leak-tightness or illumination performance that is desired. Thus, improved systems and methods for terminating fiber optic bundles are desirable.

SUMMARY

In one illustrative embodiment, a method comprises applying a frit material to a plurality of fibers in a fiber bundle. The frit material has a first melting temperature lower than a second melting temperature of the plurality of fibers in the fiber bundle. The method also comprises heating the frit material at a temperature between the first melting temperature and the second melting temperature to bind the frit material to the plurality of fibers without melting the plurality of fibers in the fiber bundle and to create a seal between the plurality of fibers.

In another illustrative embodiment, an apparatus comprises a fiber bundle and a frit material. The fiber bundle is comprised of a plurality of fibers extending within the housing, wherein tips of the plurality of fibers are exposed at an end portion of the housing. The frit material forms a hermetic seal between the plurality of fibers and between the fiber bundle and an interior surface of the end portion of the housing. The frit material has a lower melting temperature than the plurality of fibers in the fiber bundle.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances well known methods, procedures, components, and circuits have not been described in detail so as not to unnecessarily obscure aspects of the embodiments.

The illustrative embodiments described below provide a method and apparatus for terminating a fiber bundle in a manner that improves the performance of the fiber bundle. In particular, the illustrative embodiments described below provide a method and apparatus for terminating a fiber bundle using a frit material. For example, an end of the fiber bundle may be potted using a frit material having a lower melting temperature than the plurality of fibers in the fiber bundle but with a similar coefficient of thermal expansion. The frit material may be heated to create a seal between the plurality of fibers in the fiber bundle. When the fiber bundle is located within a housing, the frit material may also be used to create a seal between the fiber bundle and the housing. In one illustrative embodiment, the seal may be a hermetic seal.

In one illustrative embodiment, the frit material is a glass frit comprised of glass particles. Using a glass frit to hermetically seal the end of the fiber bundle may help prevent a decrease in the level of leak-tightness and illumination performance of the potted end of the fiber bundle. For example, once heated, the glass frit may be sufficiently durable to withstand high temperatures and pressure and to seal against liquids, steam, air, or biologic intrusions.

Figure 1A:
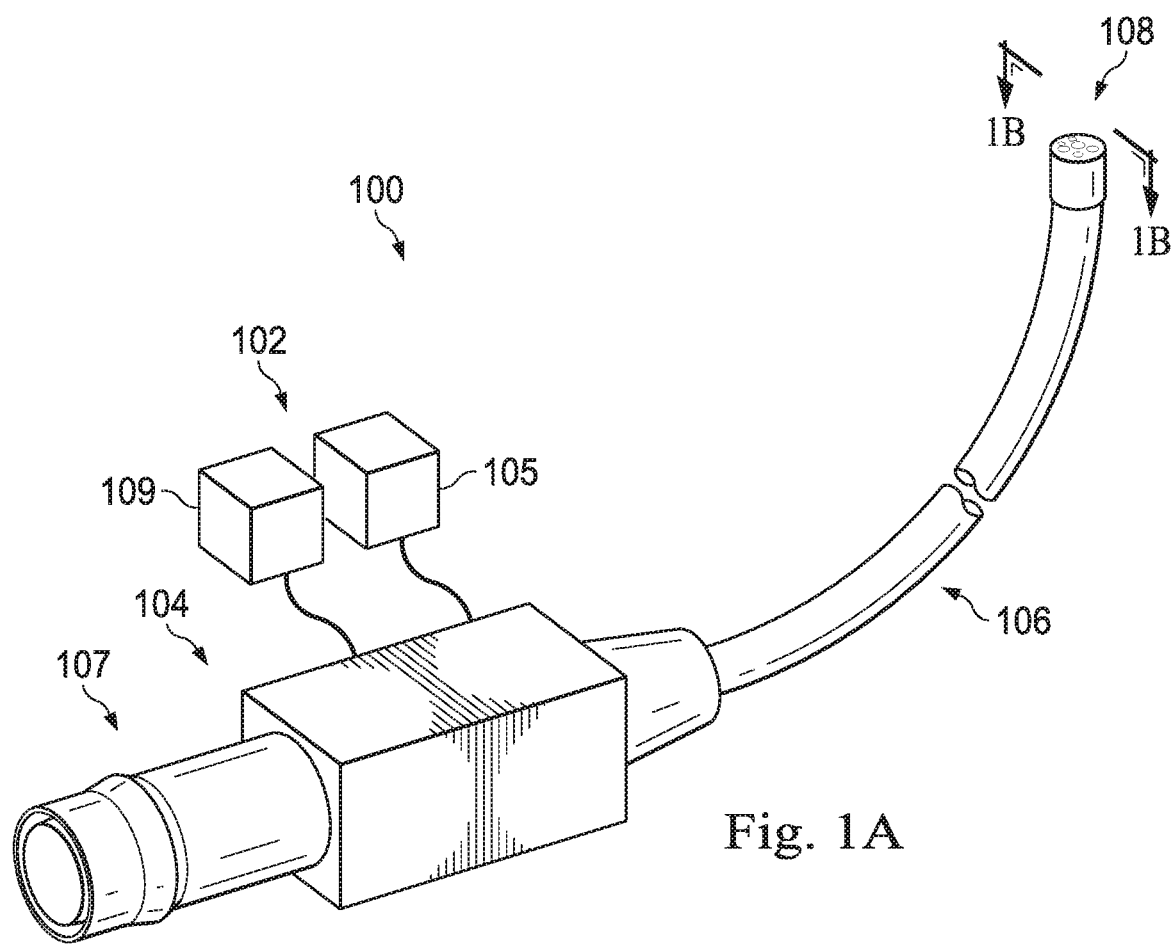
FIG. 1A is an illustration of a medical instrument in accordance with an illustrative embodiment.
Figure 1B:
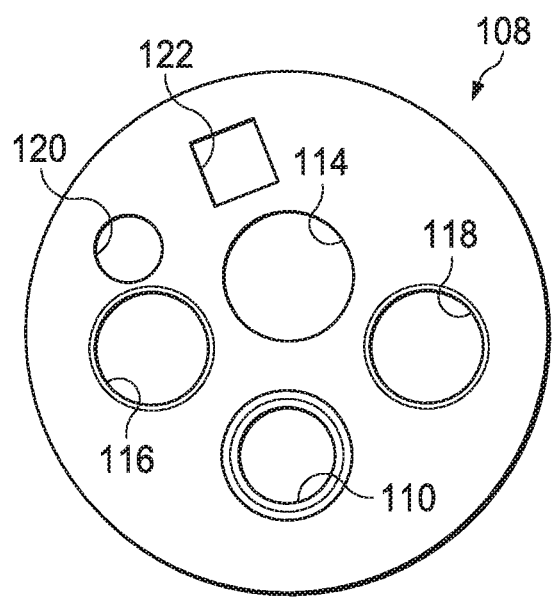
FIG. 1B is an illustration of an enlarged view of an end of an elongate member of a medical instrument in accordance with an illustrative embodiment.

Referring to FIGS. 1A and 1B of the drawings, a medical instrument 100 is depicted in accordance with an illustrative embodiment. In FIG. 1A, the medical instrument 100 is an image capture device 102 that may be used to medically inspect various internal body parts and cavities. For example, the image capture device 102 may take the form of an endoscope used to capture images that can then be viewed by a human operator using the image capture device 102.

In one illustrative embodiment, the image capture device 102 may include a body 104, a light source 105, an elongated member 106, an eyepiece 107, and an image recording device 109. The body 104 is typically kept outside of the patient anatomy during the actual inspection. The elongated member 106 may be at least partially inserted inside the body such that a distal end 108 of the elongated member 106 is positioned relative to a body part of interest. The elongated member 106 may be rigid, flexible, articulated, partially flexible, or a combination thereof. Although depicted as curved or bent for exemplary purposes, in various embodiments elongated member 106 may be straight, angled, curved, or any combination thereof. Depending on the implementation, the elongated member 106 may be comprised of metal, plastic, a combination of the two, or some other suitable material.

The elongated member 106 may include channels housing various components, which may include an illumination system 110. The illumination system 110 may direct light from the light source 105 to illuminate the portion of the patient anatomy being inspected. In other words, the illumination system 110 may direct light towards the portion of the patient anatomy at which the distal end 108 of the elongated member 106 is pointing. In this illustrative embodiment, the illumination system 110 may include a light guide. In other embodiments, the illumination system 110 may include multiple light guides, one or more other components, or a combination thereof.

The elongated member 106 may also house an optional imaging bundle 114. The imaging bundle 114 may include a fiber bundle that is used to capture and convey an image to the image recording device 109 or to the eyepiece 107 for viewing by the human operator. The fiber bundle may be, for example, a fiber optic bundle comprised of a plurality of optical fibers. The image recording device 109 may take the form of a camera or some other type of image recording device.

In FIG. 1B, an enlarged view of the distal end 108 of the elongated member 106 is shown. As depicted, the elongated member 106 may house other optional components, such as, for example, without limitation, an air tube 116, a water tube 118, a suction tube 120, a control wire 122, or a combination thereof. In other illustrative embodiments, the elongated member 106 may also house some other type of component, such as, for example, a biopsy extraction device (not shown).

Figure 2:
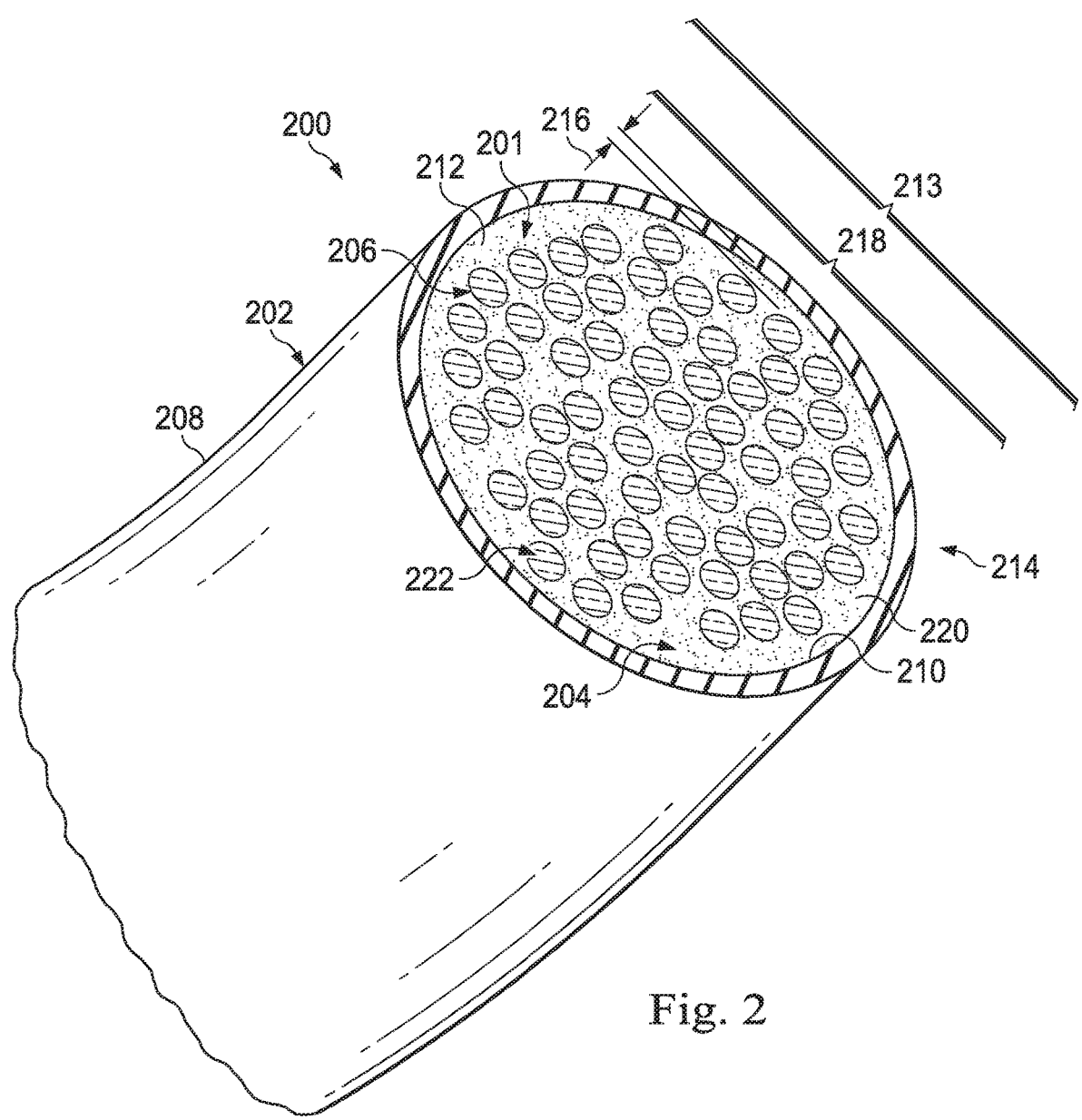
FIG. 2 is an illustration of an enlarged view of an end portion of a light guide in accordance with an illustrative embodiment.

FIG. 2 is an illustration of an enlarged view of an end portion of an optical apparatus 200. The optical apparatus 200 may be, for example, the illumination system 110 (e.g., the light guide) or the imaging bundle 114 in FIGS. 1A and 1B. The optical apparatus 200 includes a fiber bundle 201, a housing 202, and a seal 204. The optical apparatus 200 may extend within a channel of the elongated member 106 such that the housing 202 is positioned near the distal end 108 of the elongated member.

The fiber bundle 201 is comprised of a plurality of fibers 206, which may take the form of a plurality of optical fibers. Accordingly, the fiber bundle 201 may also be referred to as a fiber optic bundle. Depending on the implementation, each optical fiber in the plurality of fibers 206 may be made from silica, glass, plastic, or some other suitable material that allows the optical fiber to transmit light between the two ends of that optical fiber. The plurality of fibers 206 may include any number of optical fibers. For example, without limitation, the plurality of fibers 206 may include tens, hundreds, or thousands of optical fibers.

The housing 202 may have an outer surface 208 and an inner surface 210. The fiber bundle 201 may be located within a channel 212 defined by the inner surface 210 of the housing 202. The channel 212 may have a diameter 213 that may also be referred to as an inner diameter or internal diameter of the housing 202. In one illustrative embodiment, the housing 202 may be comprised of a metallic material.

As depicted at the end portion 214 of the housing 202, a clearance 216 is present between the housing 202 and the fiber bundle 201. This clearance 216 may help with insertion of the fiber bundle 201 through the housing 202. In this illustrative example, the clearance 216 may be the percentage difference between the diameter 213 of the channel 212 formed by the housing 202 and an outer diameter 218 of the fiber bundle 201. For example, the diameter 213 of the channel 212 may be greater than the outer diameter 218 of the fiber bundle 201 to provide a sufficient clearance 216 between the fiber bundle 201 and the inner surface 210 of the housing 202. In one illustrative embodiment, the clearance 216 desired may be at least 1 percent. For example, when the fiber bundle 201 has an outer diameter 218 of about 2.35 millimeters, the channel 212 may have a diameter 213 that is at about 2.37 millimeters or greater. In some illustrative embodiments, the clearance 216 desired may be at least 2 percent, at least 5 percent, at least 10 percent, or even up to about 30 percent.

The seal 204 is present near the end portion 214 of the housing 202. The seal 204 may bind the plurality of fibers 206 to each other and to the inner surface 210 of the housing. The seal 204 may be a barrier between the individual fibers of the plurality of fibers 206 and between the plurality of fibers 206 and the housing 202.

The seal 204 is created using a frit material. The frit material is heated to melt the frit material to bind the frit material to the plurality of fibers 206 and the inner surface 210 of the housing 202. In this illustrative embodiment, heating the frit material may be performed by firing the frit material to melt the frit material. Firing the frit material creates the seal 204 binding the plurality of fibers 206 to each other and to the inner surface 210 of the housing 202. In this manner, the seal 204 may hold the plurality of fibers 206 in a particular configuration relative to each other and to the housing 202. In this illustrative embodiment, the frit material may be a glass frit comprised of glass particles that are sufficiently durable to withstand the heating process. Further, the seal 204 formed by the glass frit may be a hermetic seal that protects against liquid, steam, air, or biologic intrusion.

As depicted in this illustrative embodiment, the optical apparatus 200 has a polished end 220. The polished end 220 of the fiber bundle 201 may be formed by both a plurality of exposed tips 222 of the plurality of fibers 206 and the seal 204. In this illustrative embodiment, the tip of each optical fiber in the plurality of fibers 206 of the fiber bundle 201 is exposed to allow illumination from the tip.

Figure 3:
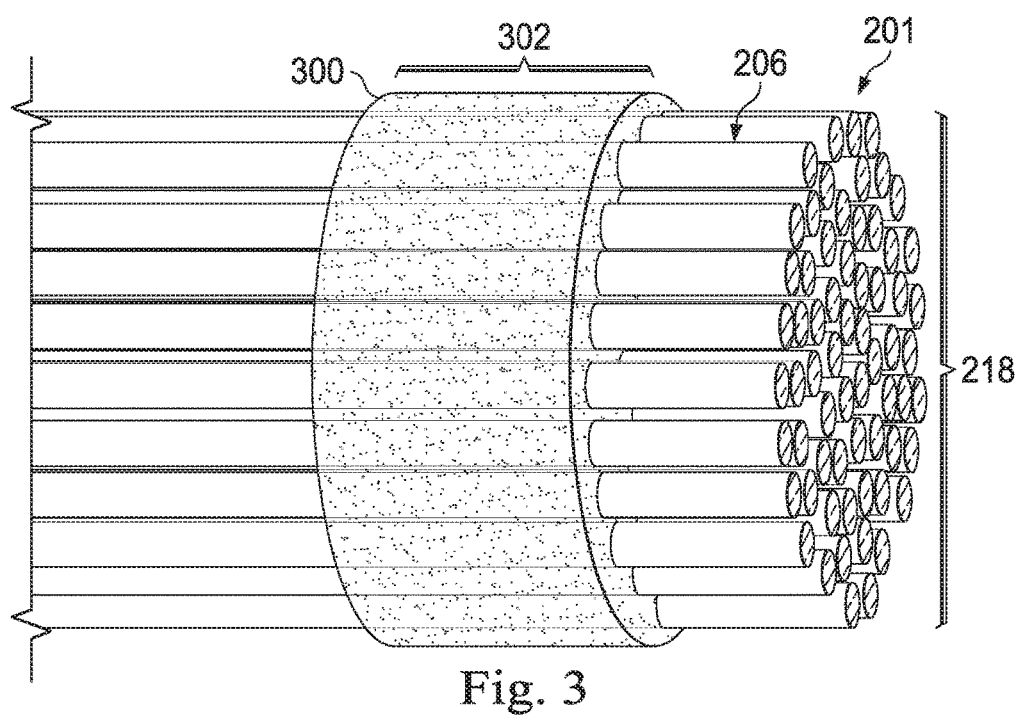
FIG. 3 is an illustration of a frit material applied to a plurality of fibers in a fiber bundle in accordance with an illustrative embodiment.
Figure 4:
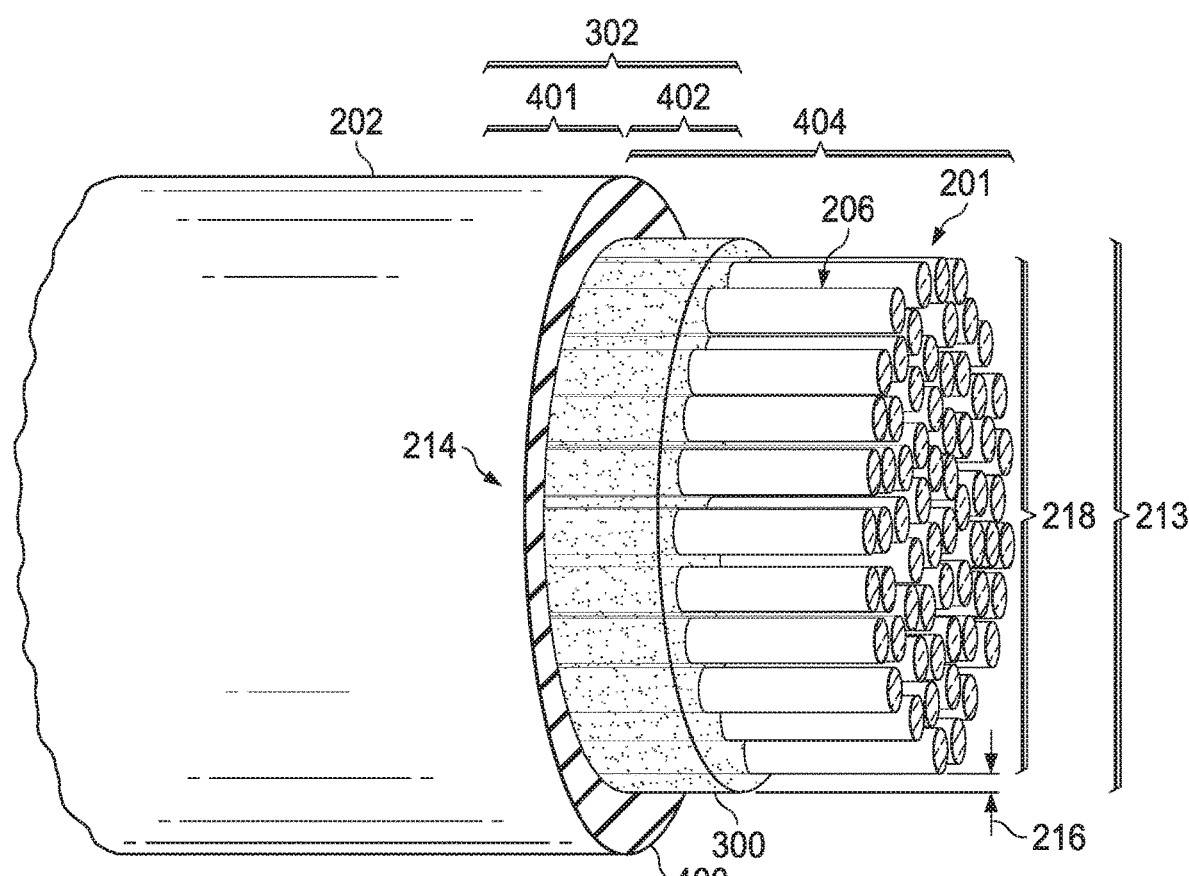
FIG. 4 is an illustration of a fiber bundle inserted within a housing in accordance with an illustrative embodiment.
Figure 5:
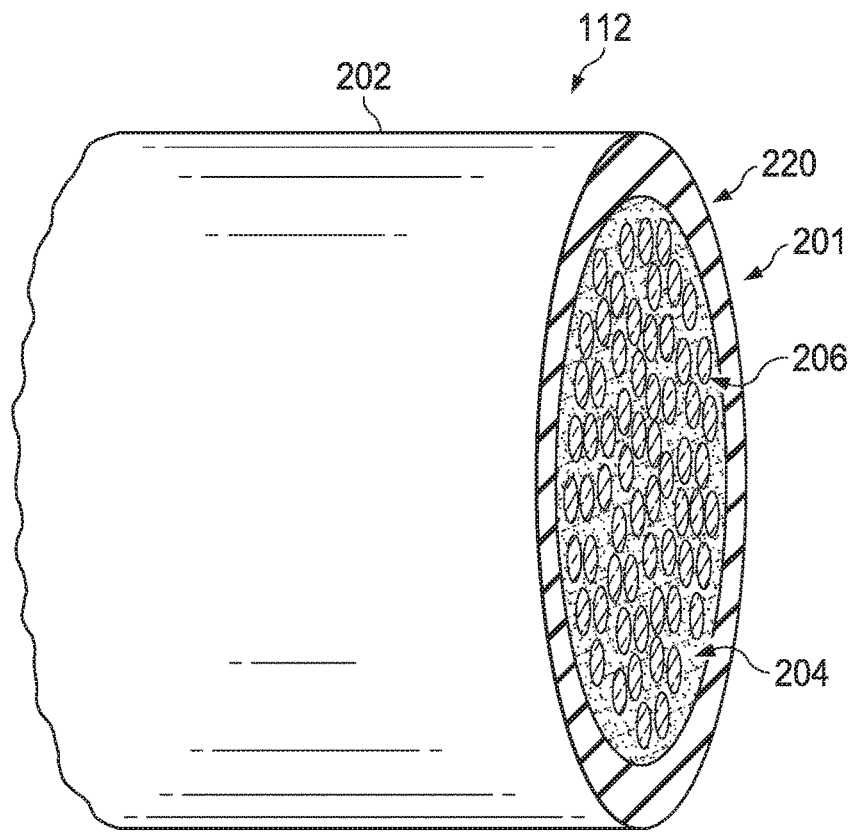
FIG. 5 is an illustration of a fiber bundle bound to a housing by a seal in accordance with an illustrative embodiment.

FIGS. 3-5 are illustrations of steps that may be used to form the seal 204 shown in FIG. 2.

Turning first to FIG. 3, an illustration of a frit material 300 applied to the plurality of fibers 206 in the fiber bundle 201 is depicted in accordance with an illustrative embodiment. As depicted, the frit material 300 has been applied to the plurality of fibers 206 in the fiber bundle 201 to form a wetted section 302 of the fiber bundle 201. In some instances, the wetted section 302 may also be referred to as a coated section.

The frit material 300 may have a lower melting temperature than the plurality of fibers 206. Further, the frit material 300 may have a first coefficient of thermal expansion that is within a predetermined range of a second coefficient of thermal expansion of the plurality of fibers 206. For example, without limitation, the plurality of fibers 206 and the frit material 300 may have coefficients of thermal expansion that are within a predetermined range of each other and between about $4 \times 10^{-10}$ $K^{-1}$ and about $9 \times 10^{-10}$ $K^{-1}$. For example, the first coefficient of thermal expansion for the frit material 300 may have a value that is between about $4 \times 10^{-10}$ $K^{-1}$ and about $9 \times 10^{-10}$ $K^{-1}$ and that value may be within 1 percent, within 2 percent, within 5 percent, or within some other predetermined range of the second coefficient of thermal expansion of the plurality of fibers 206.

The frit material 300 may be applied to the plurality of fibers 206 in a number of different ways. In one illustrative embodiment, the frit material 300 may be injected between the plurality of fibers 206. In other illustrative embodiments, the frit material 300 may be painted or brushed between the plurality of fibers 206.

In some cases, the frit material 300 may be mixed with a binder, a solvent, or both prior to applying the frit material 300 to the plurality of fibers 206. For example, the frit material 300 may be mixed with a binder to form a paste that may be more easily applied to the plurality of fibers 206. As another example, the frit material 300 may take the form of a powder that is mixed with a solvent, such as alcohol. The alcohol may be, for example, without limitation, isopropyl alcohol. The isopropyl alcohol may help in applying the frit material 300 to the plurality of fibers 206 because the surface tension of the isopropyl alcohol may help wick the particles of the frit material 300 between the plurality of fibers 206.

The length of the wetted section 302 of the fiber bundle 201 may be selected to ensure that a proper seal is formed between the plurality of fibers 206 and between the plurality of fibers 206 and the housing 202 shown in FIG. 2. As one illustrative example, the frit material 300 may be applied such that the wetted section 302 of the fiber bundle 201 has a length substantially equal to or greater than the diameter of the fiber bundle 201. For example, when the fiber bundle 201 has a diameter of about 3.2 millimeters, the wetted section 302 of the fiber bundle 201 may be at least about 3.2 millimeters or greater.

In some cases, the frit material 300 may be applied such that the wetted section 302 of the fiber bundle 201 has a length that is at least about 5 percent greater than the diameter of the fiber bundle 201. In other cases, the frit material 300 may be applied such that the wetted section 302 of the fiber bundle 201 has a length that is at least about 10 percent greater than the diameter of the fiber bundle 201.

In this illustrative embodiment, the plurality of fibers 206 may have small diameters. For example, without limitation, an optical fiber in the plurality of fibers 206 may have a diameter of about 50 micrometers. In other illustrative embodiments, each optical fiber in the plurality of fibers 206 may have a diameter of between about 20 micrometers and about 80 micrometers (or larger or smaller diameters).

The frit material 300 may be selected such that the particles of the frit material 300 have a size sufficiently small to allow the particles to easily and readily disperse between the plurality of fibers 206. In one illustrative embodiment, the frit material 300 may take the form of a glass frit that is comprised of glass particles. In one illustrative embodiment, the glass particles may have a diameter less than about 75 micrometers. In some illustrative embodiments, the glass frit may include glass particles with diameters ranging between about 5 micrometers and about 70 micrometers. In one illustrative embodiment, the glass frit used may be SCHOTT GO18-255, which is manufactured by the SCHOTT Corporation.

Once the frit material 300 has been applied to sufficiently coat the individual fibers and groups of fibers in the fiber bundle 201, the fiber bundle 201 may be ready to be inserted into the housing 202. For example, the fiber bundle 201 may be threaded into the channel 212 of the housing 202, beginning at the end portion 214 of the housing 202.

FIG. 4 is an illustration of the fiber bundle 201 inserted within the housing 202, depicted in accordance with an illustrative embodiment. The fiber bundle 201 with the wetted section 302 is inserted within the housing 202 such that the plurality of fibers 206 protrudes past an edge 400 of the end portion 214 of the housing 202. In particular, the fiber bundle 201 is inserted through the housing 202 such that at least a portion of the wetted section 302 of the fiber bundle 201 protrudes past the edge 400 of the housing 202.

For example, a first portion 401 of the wetted section 302 of the fiber bundle 201 may be located within the housing 202, while a second portion 402 of the wetted section 302 may protrude past the edge 400 of the housing 202. In one illustrative embodiment, the fiber bundle 201 may be inserted within the housing 202 such that the first portion 401 of the wetted section 302 that is located within the housing 202 has a length substantially equal to or greater than the outer diameter 218 of the fiber bundle 201. This length for the first portion 401 may help ensure that a proper seal is formed at the end portion 214 of the housing 202. A proper seal may be formed when the migration of fluid or other particles into the optical apparatus 200 is prevented or limited to within allowable tolerances. Further, the fiber bundle 201 may be inserted within the housing 202 such that a second portion 402 of the wetted section 302 that protrudes past the edge 400 of the end portion 214 of the housing 202 has a length that is at least 1 percent greater than the diameter of the fiber bundle 201. This length for the second portion 402 may help ensure that a seal is maintained at the end portion 214 of the housing 202 after the exposed end portion 404 of the fiber bundle 201 is polished down.

The clearance 216 between the housing 202 and the fiber bundle 201 may help with insertion of the fiber bundle 201 with the wetted section 302 through the housing 202. As previously described, this clearance 216 may be the percentage difference between the diameter 213 of the channel 212 of housing 202 and an outer diameter 218 of the fiber bundle 201.

In some cases, after the fiber bundle 201 with the wetted section 302 has been inserted through the housing 202, additional frit material 300 may be applied to fill any gaps between the plurality of fibers 206 or between the fiber bundle 201 and the housing 202 at the end portion 214 of the housing 202. For example, additional frit material 300 may be injected, painted, or brushed between the plurality of fibers 206, between the fiber bundle 201 and the inner surface 210 of the housing 202 at the end portion 214 of the housing 202, or both.

Although application of the frit material 300 to the fiber bundle 201 prior to insertion of the fiber bundle 201 into the housing 202 has been described, the frit material 300 may be applied after the fiber bundle 201 has been inserted into the housing 202 in other illustrative embodiments. For example, without limitation, the fiber bundle 201 may first be inserted into the housing 202 and the frit material 300 then injected, painted, or brushed between the plurality of fibers 206 and between the plurality of fibers 206 and the housing 202.

FIG. 5 is an illustration of the fiber bundle 201 bound to the housing 202 by the seal 204, depicted in accordance with an illustrative embodiment. The frit material 300 from FIGS. 3-4 may be heated to melt the frit material 300 and create the seal 204. For example, melting the frit material 300 binds the frit material 300 to the plurality of fibers 206 and the inner surface 210 of the housing 202, binds the plurality of fibers 206 together, and binds the plurality of fibers 206 to the housing 202.

Creating the seal 204 may include performing various steps. In one illustrative embodiment, the frit material 300 may be heated at a first predetermined temperature to off-gas any binders or solvents that were mixed in with the frit material 300. This first predetermined temperature may be, for example, between about 145 degrees Celsius and about 300 degrees Celsius, depending on the type of frit material 300 and the type of binder or solvent used. For example, the first predetermined temperature may be selected as sufficiently high to off-gas any binders or solvents but below the melting temperature of the frit material.

Once any binders or solvents have been sufficiently off-gassed, one or more heating cycles may be performed. Each heating cycle may include, for example, without limitation, a firing step and a cooling step. In other illustrative embodiments, each heating cycle may include only the firing step.

The firing step includes firing the frit material 300 at a second predetermined temperature to bind the frit material 300 to the plurality of fibers 206 and to the housing 202. This second predetermined temperature may be, for example, between about 470 degrees Celsius and about 515 degrees Celsius, depending on the type of frit material 300. For example, the second predetermined temperature may be selected as higher than the melting temperature of the frit material 300 but sufficiently below the melting temperature of the plurality of fibers 206 to prevent any degradation of the plurality of fibers 206. As one illustrative example, the frit material 300 may be fired using an autoclave oven set to a temperature of about 490 degrees Celsius for about 15 minutes. This firing step causes the frit material 300 surrounding the various individual fibers and groups of fibers in the fiber bundle 201 to melt and form the seal 204 that binds the plurality of fibers 206 together and to the housing 202.

The cooling step of the heating cycle may include, for example, allowing the seal 204 to be cooled such that the presence of any voids within the seal 204 may be identified. Depending on the implementation, the seal 204 may be cooled actively using a device or passively without the use of any devices. If any voids are identified within the seal 204, the heating cycle may be repeated. Any number of heating cycles may be performed until the seal 204 meets selected criteria for the seal 204.

In one illustrative embodiment, the selected criteria may include that the seal 204 is a hermetic seal 501 with no voids. The hermetic seal 501 may prevent any liquid, air, steam, or biologic intrusion. In other illustrative embodiments, the selected criteria may be that the percentage of voids found within the seal 204 is less than a selected threshold. This selected threshold may be, for example, about 2 percent voids. In other illustrative embodiments, the selected threshold may be 0.5 percent voids. In still other illustrative embodiments, the selected threshold may be 0.01 percent voids.

Once the seal 204 has been properly formed, the exposed end portion 404 (shown in FIG. 4) of the fiber bundle 201 near the end portion 214 of the housing 202 may be polished down to form polished end 220. This polishing may be performed using currently available polishing equipment and currently known polishing processes. In this illustrative embodiment, the polished end of the fiber bundle protrudes just past the edge 400 of the housing 202.

The illustrations of the medical instrument 100 in FIGS. 1A and 1B, the housing 202 in FIGS. 1A, 1B, and 2 and FIGS. 4-5, the fiber bundle 201 in FIGS. 2-5, and the frit material 300 in FIGS. 3-5 are not meant to imply physical or architectural limitations to the manner in which the different illustrative embodiments may be implemented. Other components in addition to or in place of the ones illustrated may be used. Some components may be optional.

For example, in some illustrative embodiments, the elongated member 106 housing the light guide may house multiple light guides. In other illustrative embodiments, the housing 202 may be comprised of a material other than metal. Further, although the polished end 220 of the fiber bundle is shown protruding just past the edge 400 of the housing 202 in FIG. 5, the polished end 220 may be polished down to align with the edge 400 of the housing 202 in other illustrative embodiments.

Figure 6:
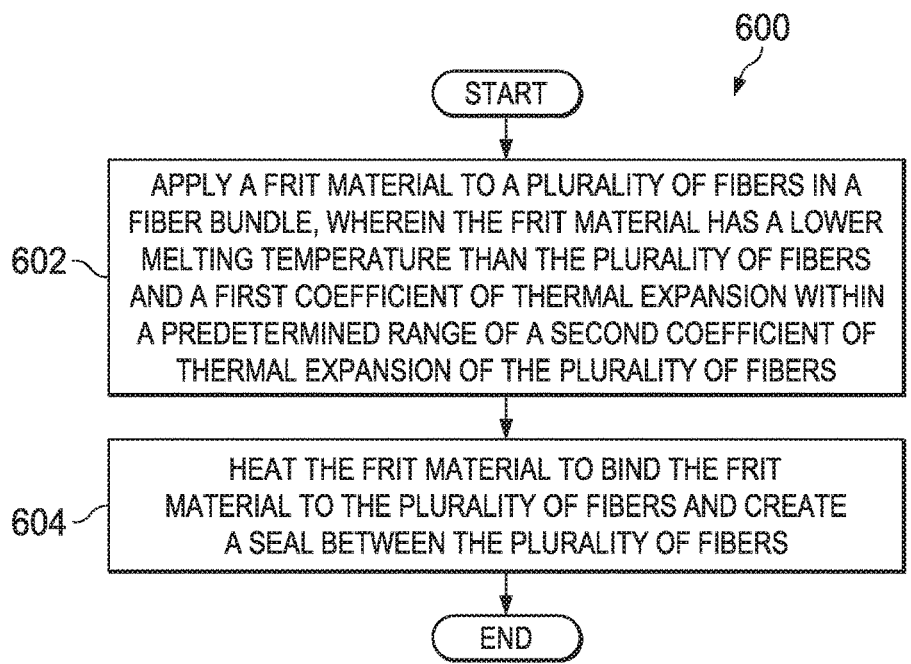
FIG. 6 is an illustration of a process for forming a seal between a plurality of fibers in a fiber bundle, depicted in accordance with an illustrative embodiment.

FIG. 6 is an illustration of a method for forming a seal between a plurality of fibers in a fiber bundle, depicted in accordance with an illustrative embodiment. The method 600 illustrated in FIG. 6 may be used to form a seal between a plurality of fibers, such as the seal 204 formed between the plurality of fibers 206 in the fiber bundle 201 described in previous figures. Although the seal may be formed at the end of a fiber bundle as previously illustrated, the method of this disclosure may be used (with or without polishing) to seal fiber bundles within fiber connectors, terminators or other optical fixtures. In some embodiments, the fibers of the fiber bundles may be sealed to one another without extending the fibers within a housing or other terminating fixture. The method 600 is illustrated as a set of operations or processes 602-604. Not all of the illustrated processes 602-604 may be performed in all embodiments of method 600. Additionally, one or more processes that are not expressly illustrated in FIG. 6 may be included before, after, in between, or as part of the processes 602-604. In some embodiments, one or more of the processes 602-604 are optional and may be omitted.

The method 600 may begin with a process 602 that includes applying a frit material to a plurality of fibers in a fiber bundle, wherein the frit material has a lower melting temperature than the plurality of fibers and a first coefficient of thermal expansion within a predetermined range of a second coefficient of thermal expansion of the plurality of fibers. The frit material may be, for example, a glass frit that is comprised of glass particles. The plurality of fibers may be, for example, a plurality of optical fibers. In process 602, the frit material may be applied to the plurality of fibers in a number of different ways.

In one illustrative embodiment, the fiber bundle may be located within a housing. The fiber bundle may protrude past an edge of an end portion of the housing. In other words, a tip of each of the plurality of fibers in the fiber bundle may extend past an edge of the end portion of the housing. In this example, the frit material may be injected between the plurality of fibers at the end portion of the housing to sufficiently coat the plurality of fibers and form a barrier between the plurality of fibers. Further, the frit material may be injected between the plurality of fibers and an interior surface of the housing to form a barrier between the plurality of fibers and the interior surface of the housing.

In another illustrative embodiment, the frit material may be applied to the plurality of fibers before the fiber bundle is inserted through the housing. For example, the frit material may be injected or brushed between the plurality of fibers of the fiber bundle to form a barrier between the plurality of fibers. The fiber bundle may then be passed through the housing such that an end of the fiber bundle protrudes past the edge of the end portion of the housing. The frit material forms a barrier between the fiber bundle and the housing. If any gaps are present, additional frit material may be injected or brushed between the plurality of fibers at the end portion of the housing.

In still other illustrative embodiments, the fiber bundle is not inserted through any housing. Rather, in process 602, the frit material is applied between the plurality of fibers of the fiber bundle and around the fiber bundle to form a thick coating around the fiber bundle.

At process 604, the frit material is heated to bind the frit material to the plurality of fibers and create a seal between the plurality of fibers. In process 604, the frit material is heated at a temperature that is above the melting temperature of the frit material but below the melting temperature of the plurality of fibers.

In one illustrative embodiment, the heating in process 604 is performed by firing the frit material using an autoclave. With respect to process 604, when the fiber bundle is located within a housing, firing the frit material also binds the plurality of fibers to the housing. The frit material has a lower melting temperature than the housing. Accordingly, in process 604, the frit material is fired at a temperature that is below the melting temperature of both the plurality of fibers and the housing.

The frit material has a first coefficient of thermal expansion that is within a predetermined range of a third coefficient of thermal expansion of the housing. In one illustrative embodiment, the housing may be comprised of one or more metallic materials selected to provide a third coefficient of thermal expansion for the housing within the desired range. For example, without limitation, the housing may be comprised of a nickel-cobalt ferrous alloy, stainless steel, some other type of metal or metal alloy, or a combination thereof. The stainless steel may be, for example, 17-4 stainless steel, 420 stainless steel, or some other grade of stainless steel. In one illustrative embodiment, when the first coefficient of thermal expansion for the frit material is between about $4\times10^{-10}$ $K^{-1}$ and about $9\times10^{-10}$ $K^{-1}$, the third coefficient of thermal expansion may be between about $5\times10^{-10}$ $K^{-1}$ and about $12\times10^{-10}$ $K^{-1}$.

Figure 7:
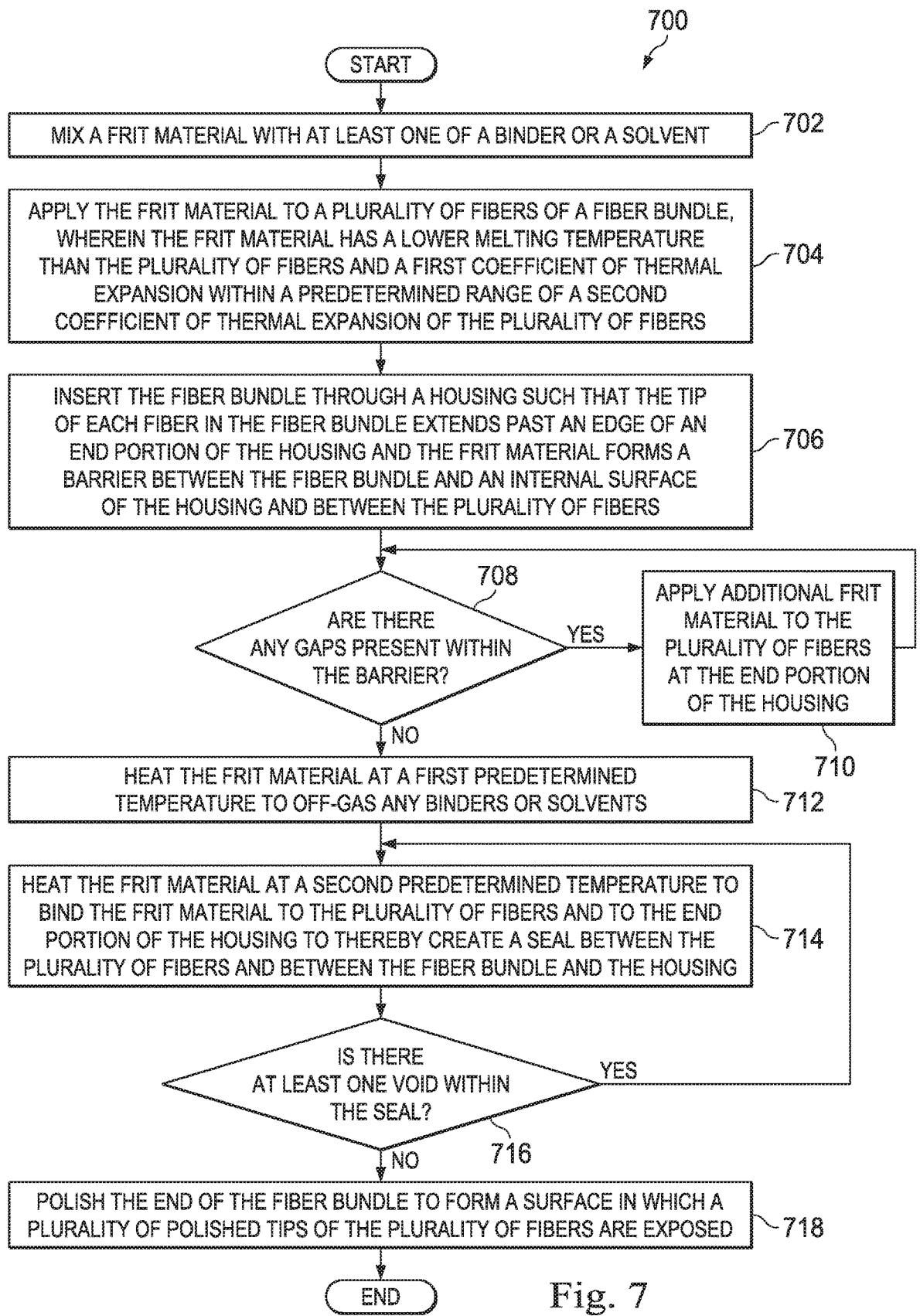
FIG. 7 is an illustration of a process for forming a seal between a plurality of fibers in a fiber bundle in accordance with an illustrative embodiment.

FIG. 7 is an illustration of a method for forming a seal between a plurality of fibers in a fiber bundle, depicted in accordance with an illustrative embodiment. The method 700 illustrated in FIG. 7 may be used to form a seal between a plurality of fibers, such as the seal 204 formed between the plurality of fibers 206 in the fiber bundle 201 described in previous figures. The method 700 is illustrated as a set of operations or processes 702-718. Not all of the illustrated processes 702-718 may be performed in all embodiments of method 700. Additionally, one or more processes that are not expressly illustrated in FIG. 7 may be included before, after, in between, or as part of the processes 702-718. In some embodiments, one or more of the processes 702-718 are optional and may be omitted.

The method 700 may begin at a process 702 by mixing a frit material with at least one of a binder or a solvent. In one illustrative embodiment, the frit material may be mixed with isopropyl alcohol. In process 702, the frit material may be mixed with at least one of a binder or a solvent to form a paste that can be more easily handled.

Next, at process 704, the frit material is applied to a plurality of fibers of a fiber bundle, wherein the frit material has a lower melting temperature than the plurality of fibers and a first coefficient of thermal expansion within a predetermined range of a second coefficient of thermal expansion of the plurality of fibers. In process 704, the frit material may be applied to the plurality of fibers by injecting, painting, or brushing the frit material between the plurality of fibers. In particular, the frit material may be applied to an end of the fiber bundle to coat a tip of each of the plurality of fibers with the frit material and at least a portion of a side of each fiber near the end of the fiber bundle.

The frit material that is applied to the plurality of fibers may be selected based on an expected clearance between the fiber bundle and the housing into which the fiber bundle is to be inserted. For example, the lower the expected clearance, the smaller the size of frit particles that may need to be used.

At process 706, the fiber bundle is inserted through a housing such that the tip of each fiber in the fiber bundle extends past an edge of an end portion of the housing and the frit material forms a barrier between the fiber bundle and an internal surface of the housing and between the plurality of fibers. At process 708, a determination may be made as to whether any gaps are present within the barrier. At process 710, if any gaps are present, additional frit material is applied to the plurality of fibers at the end portion of the housing with the method then returning to process 708.

If no gaps are present, then at process 712, the frit material is heated at a first predetermined temperature to off-gas any binders or. In process 712, the frit material may be heated at a temperature between, for example, without limitation, about 140 degrees Celsius to about 160 degrees Celsius. At process 714, the frit material is heated at a second predetermined temperature to bind the frit material to the plurality of fibers and to the end portion of the housing to thereby create a seal between the plurality of fibers and between the fiber bundle and the housing. In process 714, the frit material may be, for example, without limitation, fired at a temperature between about 480 degrees Celsius and about 500 degrees Celsius. The temperature and duration of firing may depend on the type of frit material used.

At process 716, a determination is then made as to whether at least one void is present within the seal. If at least one void is present, the method returns to process 714 described above. If no voids are present, then at process 718, the end of the fiber bundle is polished to form a surface in which a plurality of polished tips of the plurality of fibers are exposed, with the process terminating thereafter. In process 718, the polishing process may not reduce the performance or leak-tightness of the seal beyond selected tolerances.

The method 600 described in FIG. 6 and the method 700 described in FIG. 7 may be examples of the possible implementations for the apparatuses and methods in the illustrative embodiments. In alternative implementations, the steps described in these processes may occur out of the order shown. For example, without limitation, two steps shown in succession may be executed substantially concurrently, the steps may be performed in reverse order, or additional steps may be added.

While certain exemplary embodiments of the invention have been described and shown in the accompanying drawings, it is to be understood that such embodiments are merely illustrative of and not restrictive on the broad invention. Additionally, it is to be understood that the embodiments of the invention are not be limited to the specific constructions and arrangements shown and described, since various other modifications may occur to those ordinarily skilled in the art.

Further, in the detailed description of the embodiments of the invention, numerous specific details have been set forth in order to provide a thorough understanding of the disclosed embodiments. However, it will be obvious to one skilled in the art that the embodiments of this disclosure may be practiced without these specific details. In some instances, well known methods, procedures, and components have not been described in detail so as not to unnecessarily obscure aspects of the embodiments of the invention.

What is claimed is:

1. An apparatus comprising:
   a housing comprising a metallic material having a first melting temperature;
   a fiber bundle extending through the housing, wherein the fiber bundle is comprised of a plurality of fibers having a second melting temperature, and wherein an end of each fiber of the plurality of fibers in the fiber bundle extends past an edge of an end portion of the housing;
   a first seal between the plurality of fibers themselves; and
   a second seal between the plurality of fibers and an inner surface of the housing,
   wherein each of the first and second seals comprises a glass material having a third melting temperature that is lower than the first and second melting temperatures, wherein the second seal is configured to be formed as a result of the fiber bundle being inserted into the housing, and wherein the glass material coats:
   a tip of each fiber of the plurality of fibers; and
   at least a portion of a side of each fiber of the plurality of fibers near an end of the fiber bundle.

2. The apparatus of claim 1, wherein the plurality of fibers is a plurality of optical fibers.

3. The apparatus of claim 1, wherein the glass material is a glass frit.

4. The apparatus of claim 3, wherein the glass frit has a coefficient of thermal expansion that is within approximately 1 percent and 5 percent of a coefficient of thermal expansion of the plurality of fibers.

5. The apparatus of claim 3, wherein the glass frit is mixed with a binder or a solvent.

6. The apparatus of claim 1, wherein each of the first and second seals is a hermetic seal.

7. The apparatus of claim 1, wherein an inner diameter of the housing is greater than an outer diameter of the fiber bundle and a clearance distance extends between the inner diameter of the housing and an outer diameter of the fiber bundle.

8. The apparatus of claim 7, wherein the second seal extends across the clearance distance between the fiber bundle and the inner surface of the housing.

9. The apparatus of claim 7, wherein the clearance distance is at least one percent of the inner diameter of the fiber bundle.

10. The apparatus of claim 7, wherein the clearance distance is at least ten percent of the inner diameter of the fiber bundle.

11. The apparatus of claim 7, wherein the clearance distance is at least thirty percent of the inner diameter of the fiber bundle.

12. The apparatus of claim 1, wherein the end of the fiber bundle is polished.

13. The apparatus of claim 12, wherein the polished end of the fiber bundle extends past the edge of the end portion of the housing.

14. The apparatus of claim 12, wherein the polished end of the fiber bundle is aligned with the edge of the end portion of the housing.

15. The apparatus of claim 1, further comprising a light source, wherein the fiber bundle is coupled to the light source.

16. The apparatus of claim 1, further comprising an image recording device, wherein the fiber bundle is configured to convey an image to the image recording device.

17. The apparatus of claim 1, further comprising additional glass material on the plurality of fibers located at the end portion of the housing.

18. The apparatus of claim 1, wherein each of the first and second seals further comprises a binding material mixed with the glass material, wherein the binding material has a fourth melting temperature lower than the third melting temperature of the glass material.

19. The apparatus of claim 18, wherein the binding material increases a distribution of the glass material among the plurality of fibers.

20. The apparatus of claim 1, wherein each of the first and second seals is free of voids.

* * * * *